(12) United States Patent
Bavikar et al.

(10) Patent No.: US 6,979,749 B2
(45) Date of Patent: Dec. 27, 2005

(54) CATALYTIC PROCESS FOR THE PRODUCTION OF 3,3', 4,4'-TETRAMINOBIPHENYL

(75) Inventors: Sudhir Bavikar, Pune (IN); Asif Maner, Pune (IN); Ramesh Kumar Chidambaram, Pune (IN); Sudalai Arumugam, Pune (IN); Sivaram Swaminathan, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 64 days.

(21) Appl. No.: 10/811,157

(22) Filed: Mar. 29, 2004

(65) Prior Publication Data

US 2005/0215823 A1     Sep. 29, 2005

(51) Int. Cl.$^7$ ............................................. C07C 211/00
(52) U.S. Cl. ................................................... 564/309
(58) Field of Search ........................................ 564/309

(56) References Cited

U.S. PATENT DOCUMENTS

| | | | | |
|---|---|---|---|---|
| 2,895,948 A | * | 7/1959 | Brinker et al. | 528/342 |
| 3,174,947 A | * | 3/1965 | Marvel et al. | 528/331 |
| 5,317,078 A | * | 5/1994 | Connell et al. | 528/210 |
| 6,187,231 B1 | * | 2/2001 | Sansone et al. | 264/41 |

* cited by examiner

*Primary Examiner*—Samuel Barts
(74) *Attorney, Agent, or Firm*—Nixon Peabody LLP; Donald R. Studebaker

(57) ABSTRACT

This invention relates to a process for the production of 3,3',4,4'-tetraminobiphenyl (TAB) of formula (1) from non-carcinogenic raw materials, employing Suzuki type biaryl coupling as the key step. More particularly, it relates to a three steps process for the production of TAB comprising biaryl aryl coupling of 2-nitro-4-bromoacetamide (NBA) of formula (2) catalyzed by sulfilimine based palladacycles as catalysts followed by the basic hydrolysis of acetyl group and the reduction of nitro groups with conventional reducing agents.

8 Claims, No Drawings

CATALYTIC PROCESS FOR THE PRODUCTION OF 3,3', 4,4'-TETRAMINOBIPHENYL

FIELD OF THE INVENTION

This invention relates to a process for the production of 3,3',4,4'-tetraminobiphenyl (TAB) of formula (1)

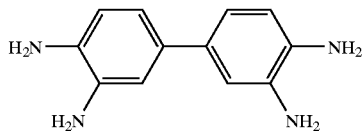

Formula-1 from non-carcinogenic raw materials, employing Suzuki type biaryl coupling as the key step. More particularly, it relates to a three steps process for the production of TAB comprising biaryl aryl coupling of 2-nitro-4-bromoacetamide (NBA) of formula (2)

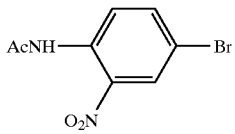

Formula 2 catalyzed by sulfilimine based palladacycles as catalysts followed by the basic hydrolysis of acetyl group and the reduction of nitro groups with conventional reducing agents.

BACKGROUND OF THE INVENTION 3,3',4,4'-Tetraminobiphenyl (TAB) is a valuable intermediate and final product in various areas. For example, TAB is used as monomer in the preparation of polybenzimidazole (PBI) polymers, which are characterized by excellent thermal and mechanical stability. The PBI polymers are widely used as proton-conducting materials for fuel cell applications (compare U.S. Pat. Nos. 2,895,948, 3,174,947, 5,317, 078 and 6,187,231). TAB is also used as an antioxidant and as an agent for stabilizing epoxide resins.

In the prior art, TAB was prepared by three known methods. One such known method is ammonolysis of 3,3'-dichlorobenzidine (DAB) in the presence of mainly Cu catalysts (both copper salts and elemental Cu) using aqueous $NH_3$. For example, French Patent Specification No 1,475, 631 describes such an ammonolysis of DCB, in the presence of a Cu—I salt and/or of $Cu_2O$ and $CaCl_2$ at an elevated temperature preferably 150–210° C. and under an elevated inert gas pressure. The crude TAB thus obtained is purified via its salt formation with a strong acid (yield of TAB is about 70% of theory). Subsequently, various attempts were made to obtain TAB in highly pure form and in high yields from crude TAB as shown below.

The process of U.S. Pat. No. 3,865,876 describes the improvement on the result of the method in accordance with the above mentioned French Patent Specifications by using essentially only CuCl as a catalyst in the ammonolysis of DCB. The yield of TAB of theory having purity of about 75–82% is between about 85 and 87%. This product has a Cu content of about 3–6% by weight. The process of U.S. Pat. No. 3,943,175 (CuCl/Cu powder can also be used as catalyst, in addition to CuCl) describes the purification of TAB (converting it into its sulfate by means of sulfuric acid, isolation of the sulfate and liberation there from of TAB by means of a base). The TAB thus liberated is dissolved and reprecipitated from an aqueous solution advantageously with the addition of activated charcoal and diatomaceous earth. However, the Cu content present in TAB is about 0.6 to 0.9% and the yield at most 45.7% of theory, relative to DCB employed.

The German Patent (Ger. Offen. DE 3, 111, 470) discloses the purification of crude TAB (obtained by ammonolysis process) by boiling it with $H_2O$ containing activated carbon and sodium dithionate (yield of TAB is 75.9% with $\leq 0.0005\%$ Cu content). The Japanese Patent (JP 60,158, 146) also describes the purification of TAB by refluxing the crude TAB with activated charcoal, aq. $FeCl_3$ solution and hydrazine hydrate (yield of TAB: 83.2% containing $\geq 10$ ppm Cu). Three more patents (U.S. Pat. Nos. 4,433,168 and 5,235,105 and Eur. Pat. Appl. EP 522,577) describe the purification of crude TAB (obtained from ammonolysis of DCB with copper catalyst) by crystallizing it in water in presence of 0–5% by weight of activated carbon and about 1–2% by weight of a water-soluble reducing agent (alkali metal dithionate or alkali metal sulfite) at temperature of 100–140° C. under $nitrogen_2$ atmosphere (yield of TAB: 88.2% of theory with only 10 ppm Cu).

In the second method for producing TAB, which has generated substantial interest, the starting material is benzidine which is acetylated with acetic anhydride, to form N,N-diacetylbenzidine. The latter compound is then nitrated with conc. $HNO_3$ to form 3,3'-dinitro-N,N-diacetylbenzidine which is base hydrolyzed to form 3,3'-dinitrobenzidine. This is then reduced by any of various means to form TAB [H. Vogel and C. S. Marvel, J. Poly. Sci. Part Al, 1531(1963)].

The third method describes the production of TAB from biphenyl which comprises the following six steps: (1) acetylating the biphenyl in the presence of an appropriate Friedel-Crafts catalyst to obtain 4,4'-diacetylbiphenyl (DAcB); (2) oximating the DAcB to form DAcB dioxime; (3) subjecting the dioxime to a double Beckmann rearrangement to obtain N,N-diacetylbenzidine. (DiAcBz); (4) Nitrating the DiAcBz to obtain 3,3'-dinitro-N,N'-diacetylbenzidine (DNAcBz); (5) removing the acetyl groups of the DNAcBz by basic hydrolysis to form 3,3'-dinitrobenzidine (DNB) and (6) reducing the nitro groups of DNB to form TAB (U.S. Pat. No. 5,041,666).

All the foregoing methods suffer from the following disadvantages associated with them:

1. They utilize benzidine and DCB as the raw materials, which are known carcinogens.
2. Direct ammonolysis of DCB catalyzed by copper salts requires high temperature (200–300° C.) at a pressure of 900–1000 psig making the process more hazardous from safety. Our own experience with direct ammonolysis of DCB by following the patented procedures is very disappointing to obtain TAB as it is always accompanied by tarry material.
3. In the direct ammonolysis, copper form complexes probably tightly with aryl TAB, so that liberating TAB from the complex becomes tedious.

4. In the ammonolysis process, TAB is always contaminated with triaminobiphenyl and little amount of copper, so that separation of these impurities from TAB becomes tedious.
5. In the dioximation method, the number of steps involved is six starting from expensive biphenyl raw material.

All the above methods make use of relatively expensive starting materials and the reaction conditions are harsh to carry out. Thus, any method for producing TAB utilizing a cheaper raw material, which is both safer and easier to handle, would be very desirable.

Accordingly, it is an object of the present invention to provide a novel process for the synthesis of TAB, which is substantially free of one or more of the disadvantage prior process. Another object is to provide a novel process for the synthesis of TAB of greater purity than heretofore possible.

OBJECTS OF THE INVENTION

The main object of the present invention is to provide a process for producing 3,3',4,4'-tetraminobiphenyl (TAB) from 2-nitro-4-bromoacetamide (NBA). Yet another object of the present invention is to use palladacycle as catalyst with turnover number in the range of 6 to 10.

Yet another object of the present invention is to provide process to obtain 3,3',4,4'-tetraminobiphenyl (TAB) with yield in the range of 60 to 84%.

SUMMARY OF THE INVENTION

The main objective of the present invention is to provide a process for 3,3',4,4'-tetraminobiphenyl (TAB) from 2-nitro-4-bromoacetamide (NBA), which avoids the drawbacks as detailed above. Particularly, the objective of the present invention is to demonstrate the use of palladacycle having formula (7) wherein R=H R1=Me or R=H; R1=CH(CH3)$_2$ or R=Me; R1=Me or R=Me; R1=Bn as new catalysts for the Suzuki type biaryl coupling of NBA with NAPB to obtain the important intermediate 3,3' dinitro-4,4'-diacetamidobiphenyl (DNDAcB) from which TAB was obtained by a known sequence of reactions (basic hydrolysis and reduction).

DETAILED DESCRIPTION OF THE INVENTION

Accordingly, the present invention provides a new process for the production of 3,3',4,4'-tetraminobiphenyl (TAB) of formula (1)

Formula-1

H$_2$N—⟨ ⟩—⟨ ⟩—NH$_2$
  |              |
  H$_2$N        NH$_2$ from 2-nitro-4-bromoacetamide (NBA) of formula (2), Formula 2

AcNH—⟨ ⟩—Br
      |
      O$_2$N which comprises treating 2-nitro-4-bromoacetamide (NBA) of formula (2) with nitro acetamido phenyl boronic acid (NAPB) of formula (3)

Formula 3

(OH)$_2$B—⟨ ⟩—NHAc
        |
        O$_2$N in presence of a catalysts under inert atmosphere ranging between 250–200° C. for a period of 1–10 h, performing the reaction in toluene as solvent and potassium carbonate as base. The other two relatively easy steps of hydrolysis of 3,3', dinitro-4,4', diacetamidobiphenyl (DNDAcB) of formula (4)

Formula 4

AcNH—⟨ ⟩—⟨ ⟩—NHAc
      |            |
      O$_2$N      NO$_2$ and reduction of nitro groups in 3,3', dinitro-4,4', diaminobiphenyl (DNDAB) of formula (5)

Formula 5

H$_2$N—⟨ ⟩—⟨ ⟩—NH$_2$
     |              |
     O$_2$N        NO$_2$ were carried out using sodium hydroxide and SnCl$_2$/con. HCl respectively. The reaction is shown in the FIG. 2.

FIG. 2

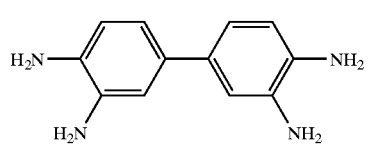 + 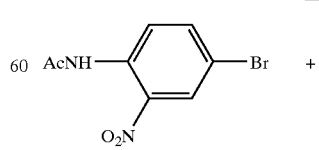

Formula 2

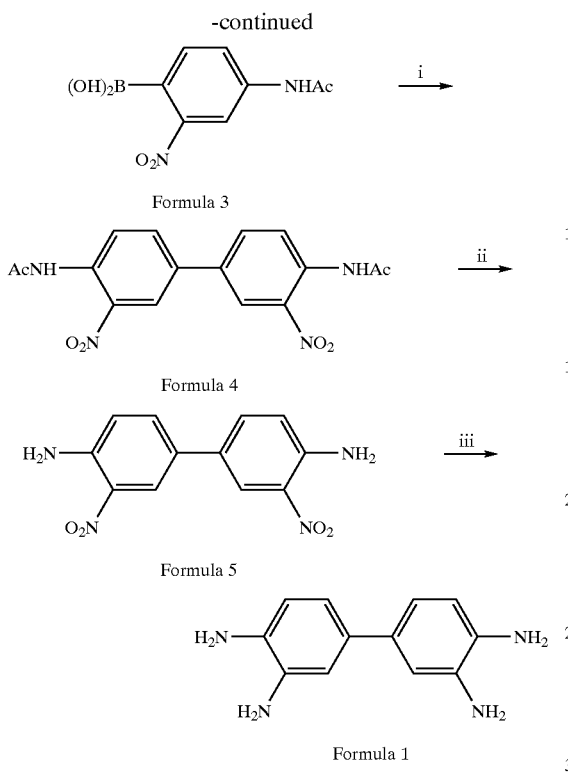

Formula 3, Formula 4, Formula 5, Formula 1

(i) Palladacycle formula (7), K$_2$CO$_3$, toluene, 110° C., 10 h; (ii) aq. NaOH, 70° C. (iii) SnCl$_2$/con. HCl, 70° C. 12 h; followed by basification.

In one of the embodiment of the present invention, palladacycles has a general formula (7) wherein when R=H; R1=Me or R=H; R1=CH(CH$_3$)$_2$ or R=Me; R1=Me or R=Me; R1=Bn are used in catalytic amounts in Suzuki type biaryl formation with a turnover number typically in the range of 6–10 million.

In another embodiment, the solvent used for all the three steps may be selected from a range of organic solvents such as, toluene, dioxane, dimethylformamide, acetonitrile, acetone, water, methanol, acetic acid and chlorinated solvents. In yet another embodiment, the reduction of nitro groups can be carried out using reducing agents such as SnCl$_2$ and conc. HCl. or H$_2$/Pd catalyst.

The process of the present invention is described herein with reference to examples, which are illustrative only and should not be construed to limit the scope of the present invention in any manner. The palladacycles (formula 7) are synthesized for the first time in our laboratory and successfully used for the Suzuki type biaryl formation reaction.

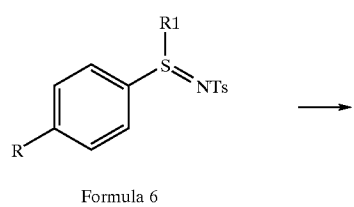

Formula 6

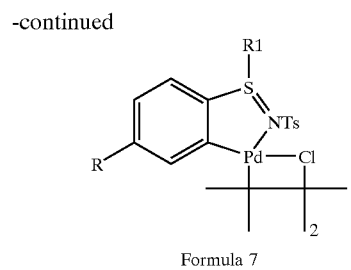

Formula 7

EXAMPLE 1

Preparation of Palladacycle where in R=H and R1=Me

Two-necked 25 ml RB flask was charged with PdCl$_2$ (0.177 g, 1 mmol), LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of the corresponding sulfilimine formula (6) (0.293 g, 1 mmol) in MeOH (2 ml). (Sulfilimine was prepared by following published procedure; Sharpless et al J. Org. Chem. 2001, 66, 594–599). The resulting reaction mixture was stirred at 25° C. for 72 h. Then distilled water (6 ml) was added to it and the solid was filtered on sintered funnel, washed with water and dried under reduced pressure (5 mm) for 3 h to afford palladacycle formula (7) where in R=H and R1=Me as brown colored solid. Yield: 66%, mp: 135–141° C. (decomp.)

EXAMPLE 2

Preparation of Palladacycle where in R=H and R1=CH(CH$_3$)$_2$

Two-necked 25 ml RB flask was charged with PdCl$_2$ (0.177 g, 1 mmol) LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of corresponding sulfilimine formula (6) (0.321 g, 1 mmol) in MeOH (2 ml). (Sulfilimine was prepared by following published procedure; Sharpless et al J. Org. Chem. 2001, 66, 594–599). The resulting reaction mixture was stirred at 25° C. for 72 h. Then distilled water (6 ml) was added to it and resulting solid was filtered on sintered funnel, washed with water and dried under reduced pressure (5 mm) for 3 h to afford palladacycle formula (7) where in R=H and R1=CH (CH$_3$)$_2$ as brown colored solid. Yield: 70%, mp: 96–98° C. (decomp.).

EXAMPLE 3

Preparation of Palladacycle where in R=Me and R1=Me

Two-necked 25 ml RB flask was charged with PdCl$_2$ (0.177 g, 1 mmol) LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of sulfilimine formula (6) (0.307 g, 1 mmol) in MeOH (2 ml).

(Sulfilimine was prepared by following published procedure; Sharpless et al J. Org. Chem. 2001, 66, 594–599). The resulting reaction mixture was stirred at 25° C. for 72 h. Then distilled water (6 ml) was added to it and resulting solid was filtered on sintered funnel, washed with water and dried under reduced pressure (5 mm) for 3 h to afford palladacycle formula (7) where in R=Me and R1=Me as brown colored solid.

Yield: 60%, mp: 78–80° C. (decomp.).

EXAMPLE 4

Preparation of Palladacycle where in R=Me and R1=Bn

Two-necked 25 ml RB flask was charged with PdCl$_2$ (0.177 g, 1 mmol) LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of sulfilimine formula (6) (0.383 g, 1 mmol) in MeOH (2 ml). (Sulfilimine was prepared by following published procedure; Sharpless et al J. Org. Chem. 2001, 66, 594–599). The resulting reaction mixture was stirred at 25° C. for 72 h. Then distilled water (6 ml) was added to it and resulting solid was filtered on sintered funnel, washed with water and dried under reduced pressure (5 mm) for 3 h to afford palladacycle formula (7) where in R=H and R1=Bn as brown colored solid.

Yield: 55%, mp: 156–159° C. (decomp.).

EXAMPLE 5

Preparation of Boronic Acid (NAPB)

The 4-bromo-2-nitroacetanilide derivative (2 g, 7.72 mmol) and 25 ml dry THF was taken in a two neck R.B. with stirring bar. The RB. was cooled up to −78° C. with the dry ice then n-BuLi (1.235 g, 19.3 mmol) was added under the atmosphere of nitrogen. This mixture was stirred for 30 min. Then trimethyl borate (2.007 g, 19.3 mmol) was added under the atmosphere of nitrogen. Then this solution was stirred for 12 h. Then unreacted n-BuLi was quenched by NH$_4$Cl solution and compound was extracted with ethyl acetate (3×50 ml). The combined extracts were concentrated under reduced pressure. The final compound was purified by column chromatography. Yield: 1.239 g (72.03%).

EXAMPLE 6

Preparation of 3,3'Dinitro-4,4'-diacetylamino biphenyl (DNDAcB)

A 25 ml two necked RB flask with double walled water condenser was charged with aryl halide (5.0 mmol), aryl boronic acid (7.5 mmol) K$_2$CO$_3$ (10 mmol), palladacycle 1(0.005 mmol) and toluene (15 ml). Then reaction mixture was heated in an oilbath at 110° C. for 10 h. (the progress of the reaction mixture was monitored by TLC). After the specified time, the reaction mixture was then allowed to cool to room temperature. The product was then isolated by pouring in to water (20 ml) and extracted with ethyl acetate (3×25 ml) The combined organic extracts were washed with water, brine and dried over anhydrous sodium sulfate and concentrated under reduced pressure to afford crude product it was then purified by column chromatography on silica gel using pet. Ether and ethyl acetate as eluent to afford the products in pure form.

EXAMPLE 7

Preparation of 3,3'-dinitro 4,4'-diaminobiphenyl (DNDAB) by Hydrolysis Procedure The 3,3'-dinitro-4,4'-diaminobiphenyl 5 g, (0.0139 mol) was suspended in 50 ml. Ethanol and 25 ml. of 10% aq. KOH solution was added to the mixture. Then it was boiled for 40 min and on cooling; crystals separated out from the red solution. The crystals were filtered, washed with water and dried. Yield: 3.201 g, (83.62%); m.p. 275° C.

EXAMPLE 8

Preparation of 3,3'-4,4'-tetraminobiphenyl (TAB) by Reduction of Nitro Groups

A mixture of 3,3'-dinitrobenzidine 2 g, (0.007 mol) and stannous chloride (6.4 g, 0.034 mol) was stirred at 0° C. in ethanol (125 ml) and con. HCl (30%) was added drop-wise over 30 min. The reaction mixture was refluxed for 10–12 h. The salt of the tetramine was precipitated out, which was basified with cold 10% NaOH solution and the solid filtered out, washed with water dried under vacuum to give TAB in 80% yield (1.249 g).

The advantages of the present inventions are

1. The unique advantages of the present process are that it employs aryl bromides and aryl boronic acids as the raw materials to make symmetrical biaryl compounds.
2. Yet anther advantages of the process is that it avoids the use of carcinogenic material such as 3,3'-dichlorobenzidine and benzidine as raw materials.
3. Yet another novelty of the process is the use of palladacycles as the new efficient catalysts for biaryl formation in high yield.
4. The turnover number of biaryl formation (Suzuki type coupling) is often in the range of 6–10 million and the conversion and the selectivity are excellent. The reaction can be conducted in water also.

We claim:

1. A process for producing 3,3',4,4'-tetraminobiphenyl (TAB) of formula 1 from 2-nitro-4-bromoacetamide (NBA) of formula 2, said process comprising the steps of

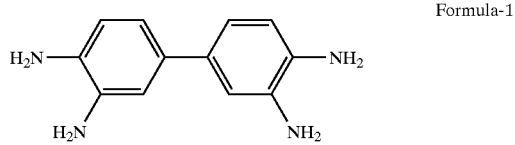

Formula-1

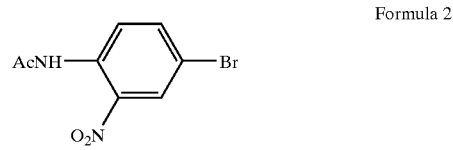

Formula 2

(a) reacting the substrate of formula 2 with nitro acetamido phenyl boronic acid (NABP) of formula 3 in the presence of a catalyst, a solvent and a base to obtain 3,3', dinitro-4,4', diacetamidobiphenyl (DNDAcB) of formula 4,

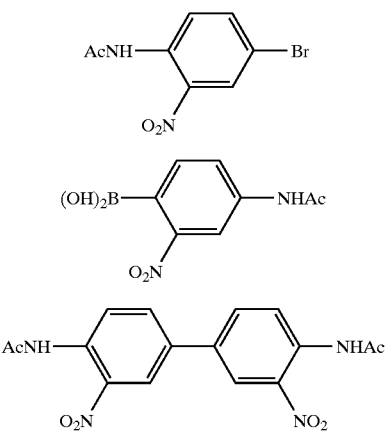

Formula 3

Formula 4

(b) hydrolyzing said 3,3', dinitro-4,4', diacetamidobiphenyl (DNDAcB) of formula 4 to obtain 3,3', dinitro-4,4', diaminobiphenyl (DNDAB) of formula 5, and

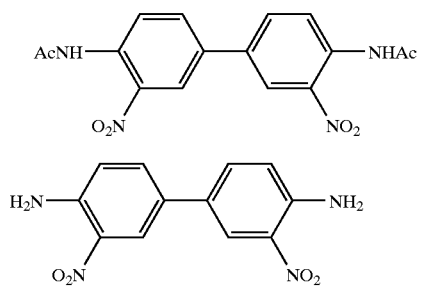

Formula 5

(c) reducing said 3,3', dinitro-4,4', diaminobiphenyl (DNDAB) of formula 5 to obtain 3,3',4-4'-tetraminobiphenyl (TAB) of formula 1.

2. The process as claimed in claim 1, wherein the reaction in step (a) is carried out under inert atmosphere ranging between 25° C.–200° C. for a period in the range of 1 to 10 hrs.

3. The process as claimed in claim 1, wherein the solvent used is selected from the group consisting of toluene, dioxane, dimethylformamide, acetonitrile, acetone, water, methanol, acetic acid and chlorinated solvents.

4. The process as claimed in claim 1, wherein the solvent and the base used in step (a) is preferably toluene and potassium carbonate respectively.

5. The process as claimed in claim 1, wherein the catalyst used is Palladacycle of formula 7 with turnover number in the range of 6–10.

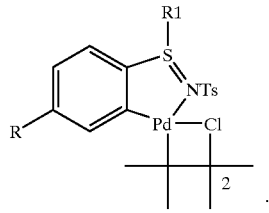

Formula-7

6. The process as claimed in claim 1, wherein the reduction is carried out using reducing agents selected from the group consisting of $SnCl_2$ with HCl and $H_2$/Pd catalyst.

7. The process as claimed in claim 1, wherein hydrolysis and reduction is carried out preferably using sodium hydroxide and $SnCl_2$/concentrated HCl respectively.

8. The process as claimed in claim 1, wherein the yield of 3,3',4,4'-tetraminobiphenyl (TAB) is in the range of 60 to 84%.

* * * * *